(12) United States Patent
Darcy et al.

(10) Patent No.: US 7,786,095 B2
(45) Date of Patent: Aug. 31, 2010

(54) AMPHIPHILIC MACROCYCLIC DERIVATIVES AND THEIR ANALOGUES

(75) Inventors: Raphael Darcy, Dublin (IE); Lawrence John Penkler, Port Elizabeth (ZA); Bart Jan Ravoo, Dublin (IE)

(73) Assignee: University College Dublin, Dublin (IE)

( * ) Notice: Subject to any disclaimer, the term of this patent is extended or adjusted under 35 U.S.C. 154(b) by 642 days.

(21) Appl. No.: 11/295,724

(22) Filed: Dec. 7, 2005

(65) Prior Publication Data

US 2006/0148756 A1 Jul. 6, 2006

Related U.S. Application Data

(63) Continuation of application No. 10/281,070, filed on Oct. 25, 2002, now abandoned, which is a continuation of application No. PCT/IE01/00057, filed on Apr. 30, 2001.

(30) Foreign Application Priority Data

Apr. 28, 2000 (IE) .............................. S2000/0326

(51) Int. Cl.
*A61K 31/724* (2006.01)

(52) U.S. Cl. ........................................ 514/58; 536/103
(58) Field of Classification Search ........................ None
See application file for complete search history.

(56) References Cited

U.S. PATENT DOCUMENTS

| | | | | |
|---|---|---|---|---|
| 4,258,180 | A | 3/1981 | Lewis et al. | 536/112 |
| 4,920,214 | A | 4/1990 | Friedman | 536/103 |
| 5,134,127 | A | 7/1992 | Stella et al. | 514/58 |
| 5,198,210 | A | * 3/1993 | Critchley et al. | 424/78.03 |
| 5,718,905 | A | 2/1998 | Skiba et al. | 424/499 |
| 5,821,349 | A | 10/1998 | Djedaini-Pilard | 536/103 |
| 6,048,736 | A | * 4/2000 | Kosak | 436/536 |

FOREIGN PATENT DOCUMENTS

| | | |
|---|---|---|
| WO | WO90/02141 | 3/1990 |
| WO | WO98/20044 | 5/1998 |

OTHER PUBLICATIONS

Duchene, D. et al "Cyclodextrin and carrier systems" J. Controlled Release (1999) vol. 62, 263-267.*
Taneva, S. et al "Association between amphiphilic cyclodextrins . . . " Langmuir (1989) vol. 5, No. 1, pp. 111-113.*
Uekama et al, CRC Critical Reviews . . . , vol. 3, Issue 1, 1987, pp. 1-40, Cyclodextrins in Drug Carrier Systems.
Zhang et al, Journal of Physical Organic Chemistry, vol. 5, 1992 pp. 518-528, Self-Organizing Systems Based on Amphiphilic . . . .
Gulik et al, Langmuir, 14, 1998, pp. 1050-1057, Structural Properties of Several Amphiphile Cyclodextrins and Some . . . .
Duchene et al, Proc. Int. Symp. Cyclodextrins, $8^{th}$, 1996, pp. 423-430, Amphiphilic Cyclodextrins and Targeting of Drugs.
Lemos-Senna et al, Proc. Int. Symp. Cyclodextrins, $8^{th}$, 1996, pp. 431-434, Release Profiles of a Hydrophobic Drug . . . .
Skiba et al, Intl. Jour. of Pharmaceutics 129, 1996, pp. 113-121, Development of a new colloidal drug carrier from . . . .
Coleman et al, Molecular Engineering for Advanced Materials, 1995, pp. 77-97, Tailoring Cyclodextrins for the . . . .
Ling et al, J. Chem. Soc. Chem. Commun., 1996, pp. 438-440, 6-S-Hydroxyethylated 6-Thiocyclodextrins: Expandable Host . . . .
Ravoo et al, Angewandte Chemie Intl Ed., vol. 39, No. 23, pp. 4324-4326, Dec. 1, 2000, Cyclodextrin Bilayer Vesicles.
Baer et al, Carbohydrate Research 228, 1992, pp. 307-314, Improved preparation of hexakis (6-deoxy) cyclomaltohexase . . . .
Takeo et al, J. Carbohydrate Chemistry, 7(2), pp. 293-308, 1988 Derivatives of α-Cyclodextrin and the Synthesis of . . . .

* cited by examiner

*Primary Examiner*—Leigh C Maier
(74) *Attorney, Agent, or Firm*—Jacobson Holman PLLC

(57) ABSTRACT

Soluble amphiphilic macrocycle analogues having lipophilic groups attached to one side of the units making up the macrocycle and hydrophilic groups attached to the other side. These amphiphilic macrocyclic derivatives have the ability to self-assemble in aqueous solvent forming micelles or vesicles and can be used as hosts for the solubilization and/or stabilization of various compounds. Embodiments of the present invention utilize macrocyclic oligosaccharides and preferably cyclodextrin as the macrocyclic derivatives to be modified.

29 Claims, 6 Drawing Sheets

US 7,786,095 B2

AMPHIPHILIC MACROCYCLIC DERIVATIVES AND THEIR ANALOGUES

This is a Continuation of application Ser. No. 10/281,070, filed Oct. 25, 2002 now abandoned, which is a continuation of PCT/IE01/00057 filed Apr. 30, 2001 and published in English.

INTRODUCTION

The present invention is directed to the production of soluble macrocyclic derivatives of a type which forms micelles and vesicles for use in encapsulation of molecules.

The invention particularly relates to soluble amphiphilic macrocyclic derivatives having lipophilic groups attached to one side of the units making up the macrocycle and hydrophilic groups attached to the other side.

Figure 1:
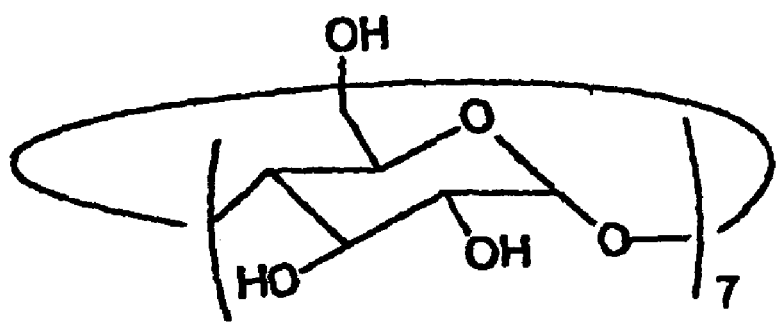

Macrocyclic oligosaccharides are typified by cyclodextrins, which are cyclic oligosaccharides composed of D-glucose residues linked together by $\alpha$-(1-4) bonds (FIG. 1). The most common examples of cyclodextrins contain six, seven or eight $\alpha$-(1-4)-linked D-glucopyranosyl units bonded together into cylinder-shaped molecules and are referred to as $\alpha$-, $\beta$-, and $\gamma$-cyclodextrins, respectively. As a consequence of the conformation of the glucopyranose units, all secondary hydroxyl groups are placed on one rim of the cylinder and all primary hydroxyl groups are placed on the other. The cylindrical interior (cavity) of the molecule is lined with hydrogen atoms and glycosidic oxygen atoms which cause it to be hydrophobic.

The cylindrical structures can be used as hosts for the inclusion of various compounds within their cavities, usually organic compounds, in the food, pharmaceutical and chemical industries. Cyclodextrins have been used to form inclusion complexes with hydrophobic molecules in which these molecules are encapsulated within the compatible hydrophobic cavity of the cyclodextrin macrocycle. This process of molecular encapsulation confers increased water solubility on the included molecule, as well as other properties such as increased stability and lowered volatility. It also allows control of the availability of the molecule, for example the bioavailability of a drug. See, e.g., Uekama et al, in CRC Critical Reviews in Therapeutic Drug Carrier Systems, Vol. 3, 1-40 (1987).

There are problems associated with the use of unmodified cyclodextrins to form inclusion complexes for the pharmaceutical industry. Widespread use of the inexpensive beta-cyclodextrin for example has been limited by its relatively low solubility in water. R. B. Friedman in U.S. Pat. No. 4,920,214 discloses how the water solubility of the cyclodextrins may be significantly increased by modification with alkylene carbonates to form hydroxyethyl ethers. Low aqueous solubility is however still a problem with many modified cyclodextrins.

A further limitation to the use of cyclodextrins as hosts for molecules, is that the hydrophobic molecules which can be included are limited by the size of the central cavity. Several attempts have been made to alter the cyclodextrin structures to enable them to encapsulate other molecules regardless of size. Cyclodextrins have been modified with lipophilic groups at the 2- and 3-positions (the secondary-hydroxyl side) of the glucose units, together with polar groups such as amino groups at the 6-positions (the primary-hydroxyl side), in order to confer amphiphilic character. Such derivatives are described by Skiba et al. in U.S. Pat. No. 5,718,905 and form monolayers, nanoparticles, and mixed lyotropic (solution) phases with other amphiphiles.

Similar derivatives with lipophilic substitution on the secondary side have been described in various reports (P. Zhang et al, Journal of Physical Organic Chemistry 1992, 5, 518-528; A. Gulik et al, Langmuir 1998, 14, 1050-1057; D. Duchene and D. Wouessidjewe, Proc. Int. Symp. Cyclodextrins, 8th, 1996, 423-430). Such derivatives are characterised by the formation of nanoparticulate aggregates which are able to trap hydrophobic or hydrophilic guest molecules to a greater or lesser extent. The entrapped guest is however instantaneously released upon contact of the nanoparticle with a solution medium (E. Lemos-Senna et al, Proc. Int. Symp. Cyclodextrins, 8th, 1996, 431-434). These systems are capable of entrapping both water-soluble and water-insoluble drugs (M. Skiba et al, International Journal of Pharmaceutics, 1996, 129, 113-121). The self-assembly properties of amphiphilic cyclodextrins have been reviewed by Coleman et al in Molecular Engineering for Advanced Materials, 1995, 77-97, Kluwer Academic Publishers (J. Becher and K. Schaumberg eds). Cyclodextrins have also been modified with lipophilic groups at the 6-positions (see C.-C. Ling, R. Darcy and W. Risse, J. Chem. Soc. Chem. Commun., 1993, 438-440). Djedaini-Pilard et al., in U.S. Pat. No. 5,821,349, describe cyclodextrins modified with alkylamino groups at the 6-position for incorporation of included hydrophobic guest molecules only into other organised surfactant systems. The heretofore described amphiphilic cyclodextrins are not soluble in water and are not capable of forming a sufficiently stable micelle or vesicle with structural properties which enable retention of entrapped molecules within the micelle or vesicle even after dilution in a solution medium.

A first object of the present invention is to modify macrocyclic derivatives typified by cyclodextrins and other macrocyclic oligosaccharides so that they are enabled by molecular self-assembly to form micelles and vesicles in aqueous solvents of their own accord giving rise to structures which enable retention of entrapped molecules within the micelle or vesicle even after dilution in a solution medium, with advantages for the delivery of therapeutic molecules. A second object of the invention is to modify the surface of the micelles or vesicles of the invention to facilitate specific attachment of the micelle or vesicle to certain cell membrane structures, with advantages for targeting and intracellular delivery of entrapped therapeutic molecules.

STATEMENTS OF INVENTION

According to the present invention there are provided soluble amphiphilic derivatives are provided having lipophilic groups attached to one side of the units forming the macrocycle and hydrophilic groups attached to the opposite side of the macrocycle characterised in that:

two or more hydrophilic groups are attached to one side of each unit forming the macrocycle; and one or more lipophilic groups are attached to the opposite side of each unit forming the macrocycle such that the number of hydrophilic groups present is always greater than the number of lipophilic groups.

The derivatives themselves preferably are oligosaccharide derivatives and even more preferably are cyclodextrin derivatives. However, in further embodiments the oligosaccharide derivatives if derived far enough are no longer saccharides but still retain a basic cyclic structure which can be utilised as derivatives according to the invention. These "non-oligosaccharide" molecules can be modified to incorporate the relative numbers of lipophilic and hydrophilic groups, described above, using the same chemical processes as are used to modify the oligosaccharide derivatives and which is described in greater detail below.

The modification of macrocyclic derivatives and it's effect can summarily be described as being achieved when at least one lipophilic group is attached to one side of a derivative forming a macrocycle and the number of hydrophilic groups on the opposite side of the unit is greater than the number of lipophilic groups present. The result of this is to provide the unit and consequently the macrocycle with amphiphilic character. However, also due to the relative numbers of hydrophilic and lipophilic groups, the amphiphilic macrocycle is soluble in aqueous solvent. Such soluble amphiphilic macrocycles have never been described before in the prior art. Thus the great advantage of amphiphiles of according to the present invention is that stable macrocycle aggregates can self-assemble in aqueous solvent, which aggregates described in greater detail below, allow the solubilisation and/or stabilisation of guest molecules.

In one particularly preferred embodiment, the lipophilic groups are attached at the 6-positions of cyclodextrin molecules, and the hydrophilic groups are attached to the 2- and 3-positions. Depending on the number and effective size of the lipophilic groups at the 6-position and the number and effective size of the hydrophilic groups at the 2- and 3-position, the resulting wedge-shaped or cylindrical macrocyclic amphiphiles (FIG. 2) self-assemble in aqueous solutions into micelles or bilayer vesicles. The micelles can encapsulate hydrophobic molecules, while the bilayer vesicles can encapsulate hydrophobic or hydrophilic molecules.

The advantage of these macrocyclic cyclodextrin derivatives, as mentioned previously, is that they spontaneously aggregate to form highly stable micelles or vesicles distinct from conventional liposomes and furthermore, they are water soluble. The unique aggregation properties of the derivatives may be usefully employed in the encapsulation of drugs including biological macromolecules such as proteins and DNA in order to enhance delivery of these therapeutic entities to their respective sites of action.

In another embodiment, the aggregates of macrocyclic derivatives encapsulate other molecules.

In another embodiment, the aggregates of macrocyclic derivatives encapsulate molecules for human or veterinary therapeutic use.

In a preferred embodiment of the invention, there is provided a macrocyclic derivative characterised in that the macrocyclic derivative is a cyclodextrin derivative of the following formula:

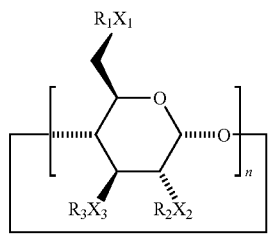

in which n equals 5-11 or higher, and indicates the number of modified glucose units in the macrocycle which may be the same or different, depending on the X- and R-groups.

$X_1$, $X_2$, $X_3$ independently, provide linking groups; in further embodiments these may independently be a simple covalent bond, or a dendrimeric group; and in further embodiments may be an atom or radical with a valency of at least two, O, S, Se, N, P, $CH_2$, $CH_2O$, carbonyl, ester, amido, amino, phosphate, sulfonyl, sulfoxide.

$R_1$ independently, provide groups which are predominantly lipophilic; examples of $R_1$ are: H, a saturated or unsaturated aliphatic or aromatic carbon or silicon radical or a halogenated version of these. Where $R_1$ is a straight or branched aliphatic chain, the number of carbons may be between 2-18. $R_1$ may be a cyclic aliphatic system such as hexyl or cholesteryl. Examples of aromatic $R_1$ are benzyl and pyridyl.

$R_2$ and $R_3$, independently, provide groups which are predominantly polar and/or capable of hydrogen-bonding. Examples of $R_2$, $R_3$ are: H, $(CH_2)_{2-4}OH$, $CH_2CH(OH)CH_2OH$, $CH_2CH(OH)CH_2NH_2$, $CH_2CH_2NH_2$; a cation such as a protonated amino group, an anion such as sulfate, sulfonato; any pharmaceutically acceptable ion; a predominantly hydrophilic group.

$R_2$, $R_3$ may be dendrimeric, and may include polymeric groups such as poly(ethylenimine) (PEI), polyamides, polyaminoacids such as polylysine; or groups which are employed because of their non-immunogenic as well as polar character, such as poly(ethylene glycol), or sialylGal-GlcNAc; or antigenic groups such as antennary oligosaccharides which are intended to stimulate the production of antibodies; or groups such as lactosyl which may be attached for the purpose of promoting adhesion of the amphiphile or of its complex with a guest molecule to specific cells or to specific proteins. Similarly other groups known in the art which are specific ligands for cellular receptors, such as folic acid, galactose, biotin, lipopolysaccharides, gangliosides, sialogangliosides, glycosphingolipids and the like may be attached to the secondary face of the modified cyclodextrins thereby expressing a targeting ligand on the external surface of the micelles or vesicles of the invention. The groups may be clustered in order to promote 'recognition' by other molecules which involves multifunctional interactions. Where these groups are polymeric or dendrimeric they may be grafted onto the amphiphile for example by living polymerisation; or the amphiphile may be a copolymer, for example it may be cross-linked by means of difunctional or polyfunctional reagents such as activated diacids or diepoxides, or copolymerised within the matrix of a polylactic or glycolic acid.

The coupling of the vesicles or micelles of the invention to antibodies may be an alternative route for targeting specific cell types. The synthetic procedures for antibody coupling are known in the art and may be applied to modified cyclodextrins of the invention which, on the secondary face provide either free amino groups for biotinylation, or free carboxylic groups for peptide coupling of an antibody via N-glutaryl detergent dialysis, or maleimide for sulfhydryl antibody coupling, or pyridyldithiopropionate for sulfhydryl and maleimide antibody coupling, or similar methods appreciated in the art.

In another embodiment, the macrocyclic derivatives are in the form bis(cyclodextrin amphiphile) in which two amphiphilic cyclodextrins of the above form share common $R_1$ groups, so as to provide 'bola amphiphiles', characterised by having two polar CD molecules joined by one or more lipophilic groups, thus: ($R_2$, $R_3$)-macrocycle-($R_1$)-macrocycle-($R_2$, $R_3$), where linker groups X are understood. In another embodiment, the bis-amphiphile is simplified to a bola amphiphile in which a common set of lipophilic groups ($R_1$) and a common macrocyclic molecule link two sets of polar headgroups ($R_2$, $R_3$), thus: ($R_2$, $R_3$)($R_1$)-macrocycle-($R_2$, $R_3$), where linker groups are understood. The advantage of such bola amphiphiles having polar groups at each end, is that a vesicle is assembled as a single layer of molecules.

In another embodiment, the groups $X_1$, or the groups $X_2$ and $X_3$, or the groups $R_1$, or the groups $R_2$ and $R_3$, may be linked to each other intramolecularly, as independent sets, by reaction of their chemical precursor groups through catalysis, or by reaction of their chemical precursor groups with a polyfunctional linking agent. An example of catalysis would be photochemical irradiation.

In another embodiment, the groups $X_1$, or the groups $X_2$ and $X_3$, or the groups $R_1$, or the groups $R_2$ and $R_3$, may be linked to each other intermolecularly, as independent sets, by reaction of their chemical precursor groups through catalysis, or by reaction of their chemical precursor groups with a polyfunctional linking reagent, to provide an oligomerised amphiphilic cyclodextrin.

In another embodiment, the macrocyclic derivative is provided wherein the units forming the macrocycle are monosaccharide units forming an oligosaccharide macrocycle with the formula:

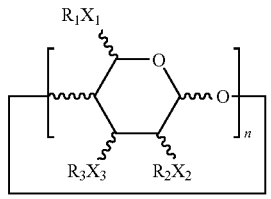

in which n equals 3-11 or higher, and indicates the number of modified monosaccharide units in the macrocycle which may be the same or different, depending on the X- and R-groups, and are linked (1-4). The groups $X_1$, $X_2$ and $X_3$, $R_1$, $R_2$ and $R_3$ have the same meanings as described above.

Examples of such macrocyclic derivatives are those in which the modified units making up the macrocycle are, independently, aglycone derivatives of L-glucose, or of D- or L-hexoses such as mannose, galactose, altrose, idose. or rhamnose ($R_1X_1$=$CH_3$), or arabinose ($R_1X_1$=H); or where the macrocycle is an oligomer of a disaccharide such as lactose.

$R_2$, $R_3$ may be dendrimeric, and may include polymeric groups such as poly(ethylenimine) (PEI), polyamides, polyaminoacids such as polylysine; or groups which are employed because of their non-immunogenic as well as polar character, such as poly(ethylene glycol), or sialylGal-GlcNAc; or antigenic groups such as antennary oligosaccharides which are intended to stimulate the production of antibodies; or groups such as lactosyl which may be attached for the purpose of promoting adhesion of the amphiphile or of its complex with a guest molecule to specific cells or to specific proteins. Similarly other groups known in the art which are specific ligands for cellular receptors, such as folic acid, galactose, biotin, lipopolysaccharides, gangliosides, sialogangliosides, glycosphingolipids and the like may be attached to the polar face of the modified oligosaccharide or oligosaccharide analogue, thereby expressing a targeting ligand on the external surface of the micelles or vesicles of the invention. The groups may be clustered in order to promote 'recognition' by other molecules which involves multifunctional interactions. Where these groups are polymeric or dendrimeric they may be grafted onto the amphiphile for example by living polymerisation; or the amphiphile may be a copolymer, for example it may be cross-linked by means of difunctional or polyfunctional reagents such as activated diacids or diepoxides, or copolymerised within the matrix of a polylactic or glycolic acid.

The coupling of the vesicles or micelles of the invention to antibodies may be an alternative route for targeting specific cell types. The synthetic procedures for antibody coupling are known in the art and may be applied to modified oligosaccharides or analogues of the invention which, on the polar face provide either free amino groups for biotinylation, or free carboxylic groups for peptide coupling of an antibody via N-glutaryl detergent dialysis, or maleimide for sulfhydryl antibody coupling, or pyridyldithiopropionate for sulfhydryl and maleimide antibody coupling, or similar methods appreciated in the art.

In another embodiment, the amphiphiles are of the form bis(amphiphile) in which two macrocyclic molecules of the above form share common $R_1$ groups, so as to provide 'bola amphiphiles', characterised by having two polar macrocycle molecules joined by one or more lipophilic groups, thus: ($R_2$, $R_3$)-macrocycle-($R_1$)-macrocycle-($R_2$, $R_3$), where linker groups X are understood. In another embodiment, the bis-amphiphile is simplified to a bola amphiphile in which a common set of lipophilic groups ($R_1$) and a common macrocyclic molecule link two sets of polar headgroups ($R_2$, $R_3$), thus: ($R_2$, $R_3$)($R_1$)-macrocycle-($R_2$, $R_3$), where linker groups are understood. A single layer of such molecules can assemble to constitute a vesicle.

In another embodiment, the groups $X_1$, or the groups $X_2$ and $X_3$, or the groups $R_1$, or the groups $R_2$ and $R_3$, may be linked to each other intramolecularly, as independent sets, by reaction of their chemical precursor groups through catalysis, or by reaction of their chemical precursor groups with a polyfunctional linking agent. An example of catalysis is photochemical irradiation.

In another embodiment, the groups $X_1$, or the groups $X_2$ and $X_3$, or the groups $R_1$, or the groups $R_2$ and $R_3$, may be linked to each other intermolecularly, as independent sets, by reaction of their chemical precursor groups through catalysis, or by reaction of their chemical precursor groups with a polyfunctional linking reagent, to provide an oligomerised amphiphile.

In another embodiment is provided, macrocyclic derivatives wherein the units making up the macrocycle are of the general formula:

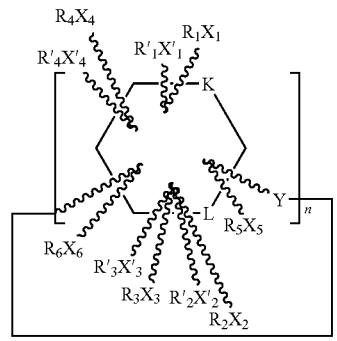

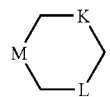

in which n equals 2-11 or higher, and indicates the number of ring units making up the macrocycle, which may be the same or different;

if any of K, L, M are zero (thus providing a unit, as part of the macrocycle, which is an open chain rather than a ring), the remaining are independently one or more of: a simple chemical bond (thus providing a five-membered ring unit as in a furanose sugar); or an atom or radical having a valency of at least 2 and can be in any position not occupied by a moiety involved in linking adjacent units forming the macrocycle, Y, which may be the same or different, are groups which link the units making up the macrocycle, such as: oxygen, sulfur, selenium, nitrogen, phosphorus, carbon, or silicon radicals having a valency of 2-4; or $OCH_2$ as in (1-2)-linked fructofuranooligosaccharides; or $OCH_2CH(OH)$ as in (1-6)-linked furanooligosaccharides; or $OCH(CH_2OH)$ as in (1-5)-linked furanooligosaccharides.

$X_1, X'_1, X_2, X'_2, X_3, X'_3, X_4, X'_4, X_5, X_6$, independently, are zero or provide linking groups for the R groups; these may be a simple covalent bond, or a dendrimeric group; other examples are: an atom or radical with a valency of at least two, $CH_2$, $CH_2O$, O, S, Se, N, P, carbonyl, ester, amido, amino, phosphate, sulfonyl, sulfoxide.

when one or more but not all of $R_1, R'_1, R_4, R'_4$, independently, is zero the remaining are groups which are predominantly lipophilic; examples are: H, a saturated or unsaturated aliphatic or aromatic carbon or silicon radical or a halogenated version of these. Where $R_1$-$R'_4$ is a straight or branched aliphatic chain, n is preferably greater than one, and the number of carbons 2-18. $R_1$-$R'_4$ may be a cyclic aliphatic system such as hexyl or cholesteryl; examples of aromatic groups are benzyl and pyridyl.

when one or more but not all of $R_2, R'_2, R_3, R'_3$, independently, is zero the remaining are groups which are predominantly polar and/or capable of hydrogen-bonding. Examples of $R_2, R_3$ are: H, $(CH_2)_{2-4}OH$, $CH_2CH(OH)CH_2OH$, $CH_2CH(OH)CH_2NH_2$, $CH_2CH_2NH_2$; a cation such as a protonated amino group, an anion such as sulfate, sulfonato; any pharmaceutically acceptable ion; a predominantly hydrophilic group.

$R_2, R'_2, R_3, R'_3$ may be dendrimeric, and may include polymeric groups such as poly(ethylenimine) (PEI), polyamides, polyaminoacids such as polylysine; or groups which are employed because of their non-immunogenic as well as polar character, such as poly(ethylene glycol), or sialylGal-GlcNAc; or antigenic groups such as antennary oligosaccharides which are intended to stimulate the production of antibodies; or groups such as lactosyl which may be attached for the purpose of promoting adhesion of the amphiphile or of its complex with a guest molecule to specific cells or to specific proteins. Similarly other groups known in the art which are specific ligands for cellular receptors, such as folic acid, galactose, biotin, lipopolysaccharides, gangliosides, sialogangliosides, glycosphingolipids and the like may be attached to the polar face of the modified oligosaccharide or oligosaccharide analogue, thereby expressing a targeting ligand on the external surface of the micelles or vesicles of the invention. The groups may be clustered in order to promote 'recognition' by other molecules which involves multifunctional interactions. Where these groups are polymeric or dendrimeric they may be grafted onto the amphiphile for example by living polymerisation; or the amphiphile may be a copolymer, for example it may be cross-linked by means of difunctional or polyfunctional reagents such as activated diacids or diepoxides, or copolymerised within the matrix of a polylactic or glycolic acid.

The coupling of the vesicles or micelles of the invention to antibodies may be an alternative route for targeting specific cell types. The synthetic procedures for antibody coupling are known in the art and may be applied to modified oligosaccharides or oligosaccharide analogues of the invention which, on the polar face provide either free amino groups for biotinylation, or free carboxylic groups for peptide coupling of an antibody via N-glutaryl detergent dialysis, or maleimide for sulfhydryl antibody coupling, or pyridyldithiopropionate for sulfhydryl and maleimide antibody coupling, or similar methods appreciated in the art.

$R_5, R_6$ are groups which may be polar or lipophilic, preferably H.

An example of such an amphiphile is that in which at least two monocyclic units making up the macrocycle are derived from a (1-1)- or (1-2)- or (1-3)- or (1-6)-linked disaccharide, or from the disaccharide sucrose, or where at least one of the units (whether cyclic or open-chain) which make up the macrocycle is derived from fructose or a furanose sugar or sialic acid or from a carbohydrate analogue (defined for this purpose as a molecule which is not a natural carbohydrate nor a derivative thereof but which can usefully function either physically or pharmaceutically as a carbohydrate).

In another embodiment, the amphiphiles are of the form bis(amphiphile) in which two amphiphilic molecules of the above form share common $R_1, R_1', R_4, R_4'$ groups, so as to provide 'bola amphiphiles', characterised by having two polar macrocycle molecules joined by one or more lipophilic groups, thus: $(R_2, R_2', R_3, R_3')$-macrocycle-$(R_1, R_1', R_4, R_4')$-macrocycle-$(R_2, R_2', R_3, R_3')$, where linker groups X are understood. In another embodiment, the bis-amphiphile is simplified to a bola amphiphile in which a common set of lipophilic groups $(R_1, R_1', R_4, R_4')$ and a common macrocyclic molecule link two sets of polar headgroups $(R_2, R_2', R_3, R_3')$, thus: $(R_2, R_2', R_3, R_3')(R_1, R_1', R_4, R_4')$-macrocycle-$(R_2, R_2', R_3, R_3')$, where linker groups are understood. A single layer of such molecules can assemble to constitute a vesicle.

In another embodiment, the groups $X_1, X'_1, X_4, X'_4$, or the groups $X_2, X'_2, X_3, X'_3$, or the groups $R_1, R'_1, R_4, R'_4$, or the groups $R_2, R'_2, R_3, R'_3$, may be linked to each other, as independent sets, intramolecularly by reaction of their chemical precursor groups through catalysis (for example through irradiation), or by reaction of their chemical precursor groups with a polyfunctional linking agent.

In another embodiment, the groups $X_1, X'_1, X_4, X'_4$, or the groups $X_2, X'_2, X_3, X'_3$, or the groups $R_1, R'_1, R_4, R'_4$, or the groups $R_2, R'_2, R_3, R'_3$, may be linked to each other, as independent sets, intermolecularly by reaction of their chemical precursor groups through catalysis, or by reaction of their chemical precursor groups with a polyfunctional linking reagent, to provide an oligomerised amphiphile.

In another embodiment, the amphiphile molecules (of any of the molecular forms or embodiments described above) self-assemble in an aqueous solvent. After self-assembly, the resulting micelles or vesicles can be transferred by physical or chemical means from the aqueous solvent into another phase, such as an aqueous phase containing a proportion of an alcohol or other polar solvent for example dimethyl formamide, dimethyl sulfoxide, tetramethylurea, dimethyl carbonate, or a polymer, or into an emulsion, or gel-like matrix, or lyophilised suspension.

In another embodiment, the assembly of amphiphile molecules may be composed of more than one of the molecular forms or embodiments described above, to provide the molecular assembly with the complementary properties of the individual amphiphiles, for example the property of cell-adhesion together with prodrug properties, or to modulate the colloidal stability of the assemblies.

In another embodiment, the amphiphile molecules may be mixed with other molecules, preferably other amphiphiles such as ceramides or glycerides, to modulate the properties of their assemblies, for example to control their colloidal stability.

In another embodiment, the amphiphile forms a complex with a therapeutic molecule for its solubilisation or stabilisation, or for its formulation into pharmaceutical compositions useful for the treatment of human or animal diseases.

In another embodiment, the drugs that complex with the amphiphile are of a lipophilic or polar nature. The drug may bind in the cavity of the macrocycle, in the lipophilic interior of the assembly, or in the aqueous internal compartment(s) of the amphiphile assembly. Examples of drugs which may be complexed with the amphiphile or which may be entrapped in the lipophilic interior of the assembly or entrapped in the aqueous internal compartment(s) of the amphiphile assembly include but are not limited to: anti-neoplastic agents (paclitaxel, doxorubicin, cisplatin, etc); anti-inflammatory agents (diclofenac, rofecoxib, celecoxib, etc); antifungals such as amphotericin B; peptides, proteins and their analogues including those to which nonpeptide groups such as carbohydrates, hemes and fatty acids are attached; oligosaccharides and their analogues such as Sialyl Lewis$^x$ analogues; oligonucleotides and their analogues; plasmid DNA; and complexes of oligonucleotides or of DNA with gene delivery agents.

In another embodiment the amphiphile is complexed with a molecule or atom used for analysis or diagnosis, for example a peptide antigen or an antibody; or a molecule used as a radiation sensitiser, for example a porphyrin.

In another embodiment the amphiphile is complexed with a molecule which functions as a prodrug, for example a precursor of nitric oxide.

In another embodiment, the amphiphile complex may be attached covalently to a polymer; the polymer may be grafted onto the amphiphile molecules of the complex for example by living polymerisation; or the amphiphile may be a copolymer, for example the amphiphile may be cross-linked by means of difunctional or polyfunctional reagents such as activated diacids or diepoxides, or copolymerised within the matrix of a polylactic or polyglycolic acid.

In another embodiment, the guest molecule is attached covalently to the amphiphile, that is, it functions as an R-group as specified above, so as to provide a precursor of the active form of the guest molecule, for example to provide a prodrug which may be biodegraded to release an active form of the drug.

In another embodiment, the amphiphile-drug complex is prepared by sonication. The advantage of this is that the complex forms smaller particles, which are easily absorbed.

In a preferred embodiment, the average particle diameter of the aggregate formed by the amphiphile of the invention is in the range of 50-500 nm.

In another embodiment, the amphiphile or its complex is present as a pharmaceutical formulation with any pharmaceutically acceptable ingredient such as a diluent, carrier, preservative (including anti-oxidant), binder, excipient, flavouring agent, thickener, lubricant, dispersing, wetting, surface active or isotonic agent which is compatible with the amphiphile or complex or aggregate of same.

In another embodiment, the amphiphile or complex is dispersed in a suitable solvent, buffer, isotonic solution, emulsion, gel or lyophilised suspension.

The amphiphile or complex is preferably administered parenterally, but may also be administered by alternative routes such as oral, topical, intranasal, intraocular, vaginal, rectal or by inhalation spray in dosage unit formulations containing conventional non-toxic pharmaceutically acceptable carriers, adjuvants and vehicles. The term parenteral as used herein includes percutaneous injections, intravenous, intramuscular, intrasteral, intrathecal, intraperitoneal injection or infusion techniques.

The present invention also provides the amphiphile or amphiphile-drug complexes in pharmaceutical formulations exhibiting sustained release of a drug. Such formulations are generally known and include devices made of inert polymers or of biodegradable polyacids or polyesters in which the active ingredient (the present amphiphile or its complex) is either dispersed, covalently linked via labile bonds, or stored as a reservoir between polymer membranes. Sustained release is achieved through diffusion of the active ingredient through the polymer matrix or hydrolysis of any covalent linkages present. Sustained release may also be attained by delivery of the active ingredient via osmotic pumps, in which the amphiphile may also act as an osmotic driving agent providing potential for the influx of water.

DETAILED DESCRIPTION

Figure 2:
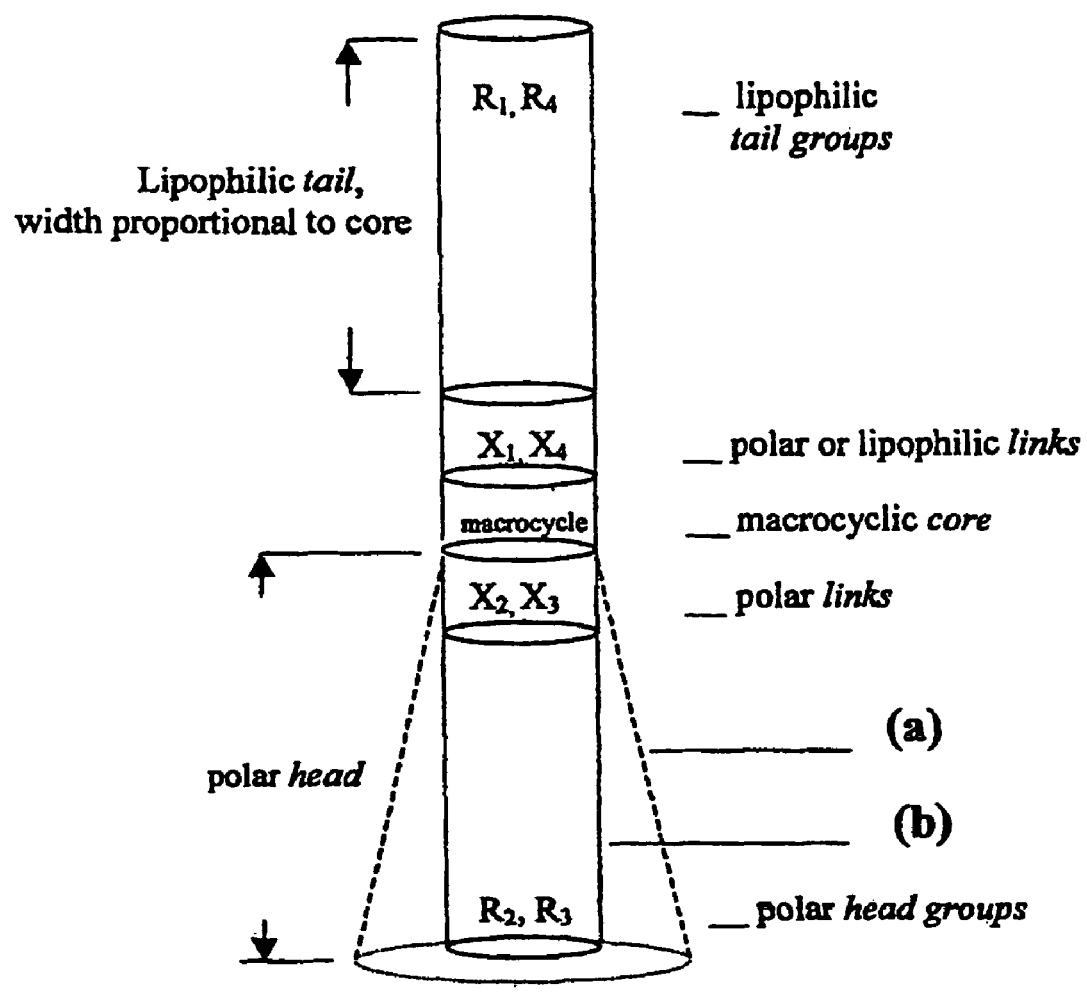
Figure 3:
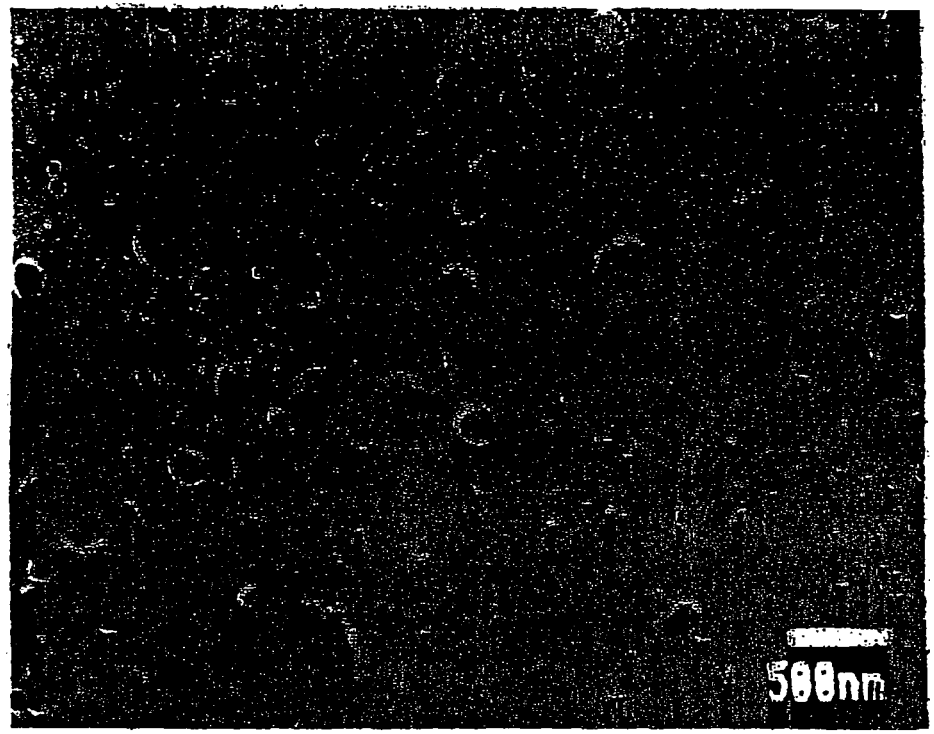
Figure 4:
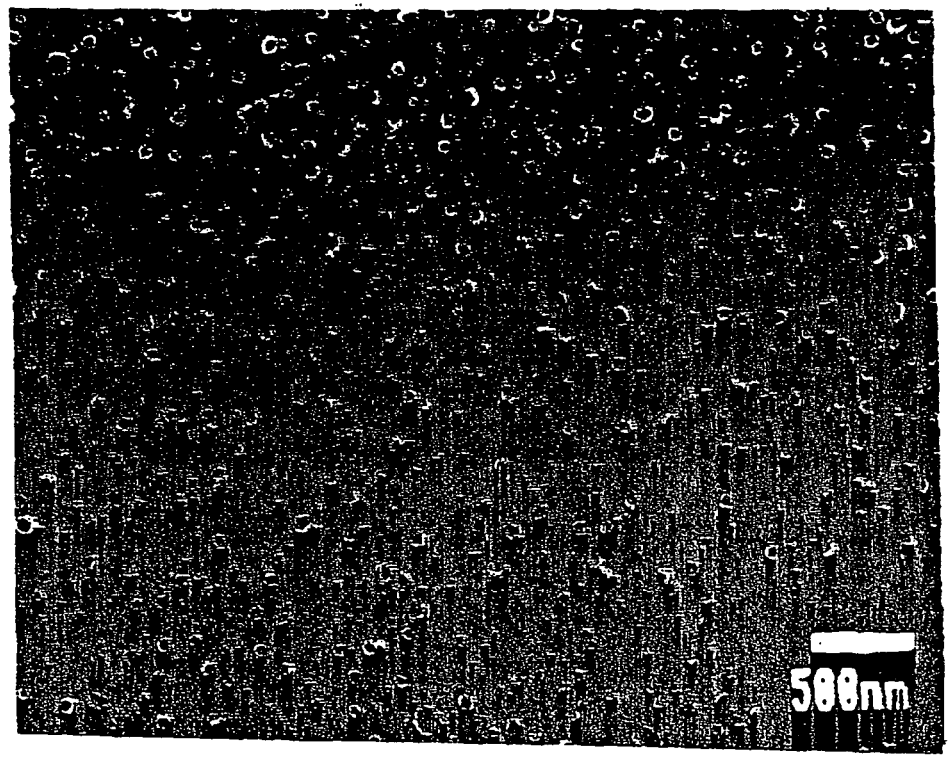
Figure 5:
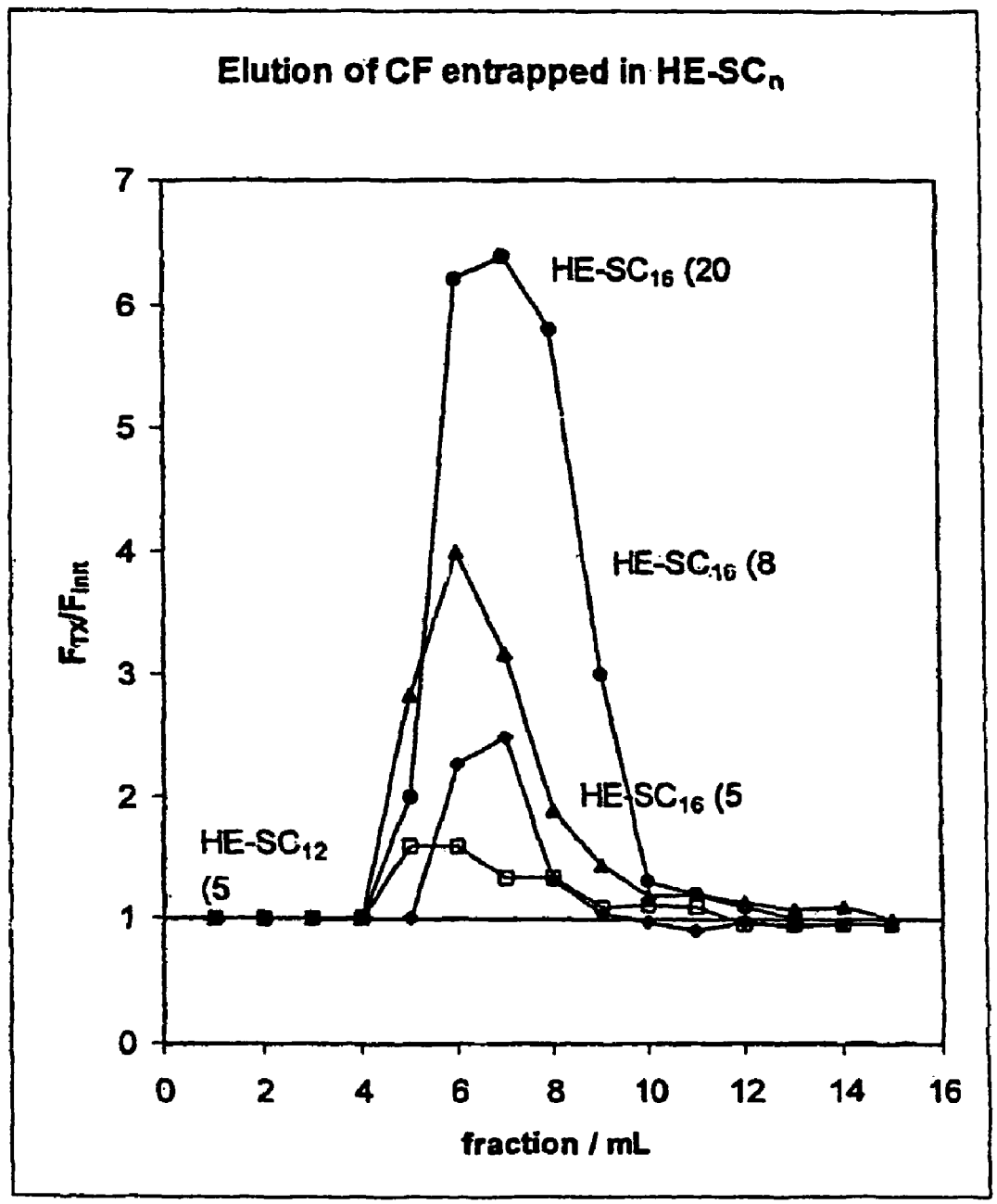
Figure 6:
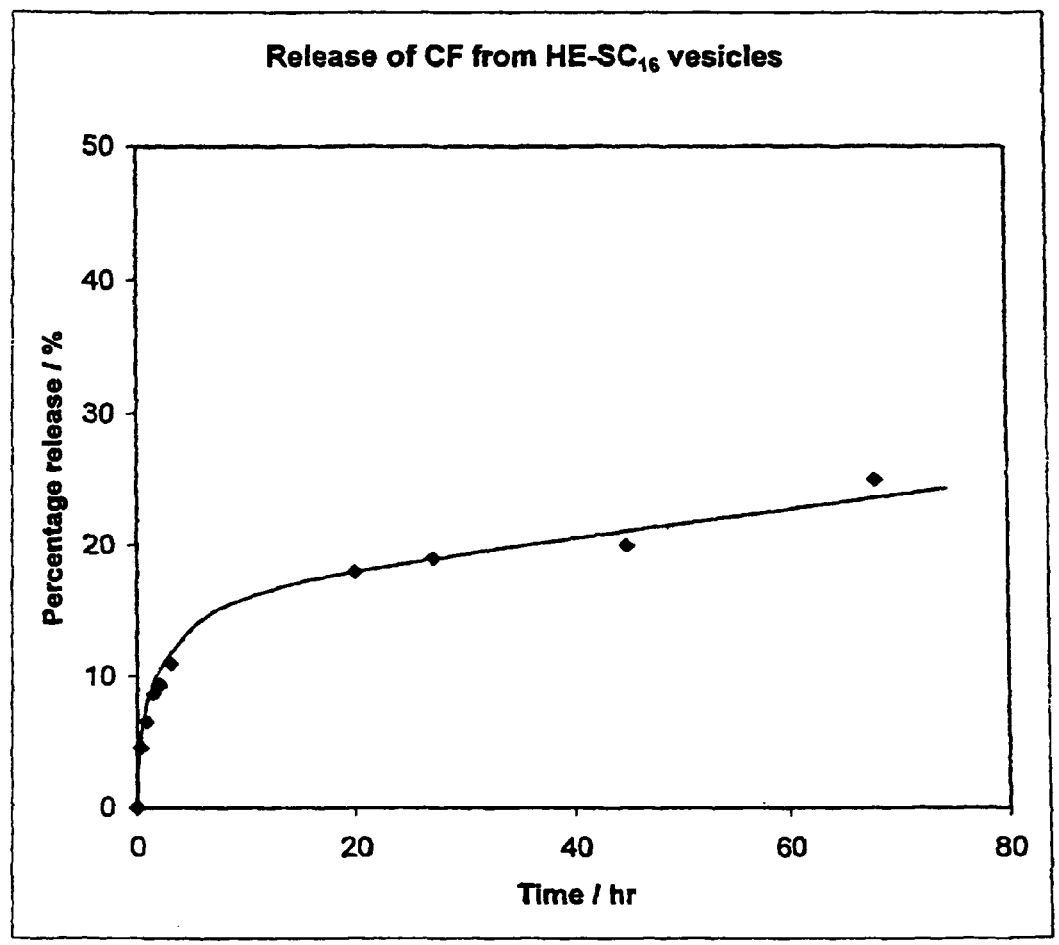
Figure 7:
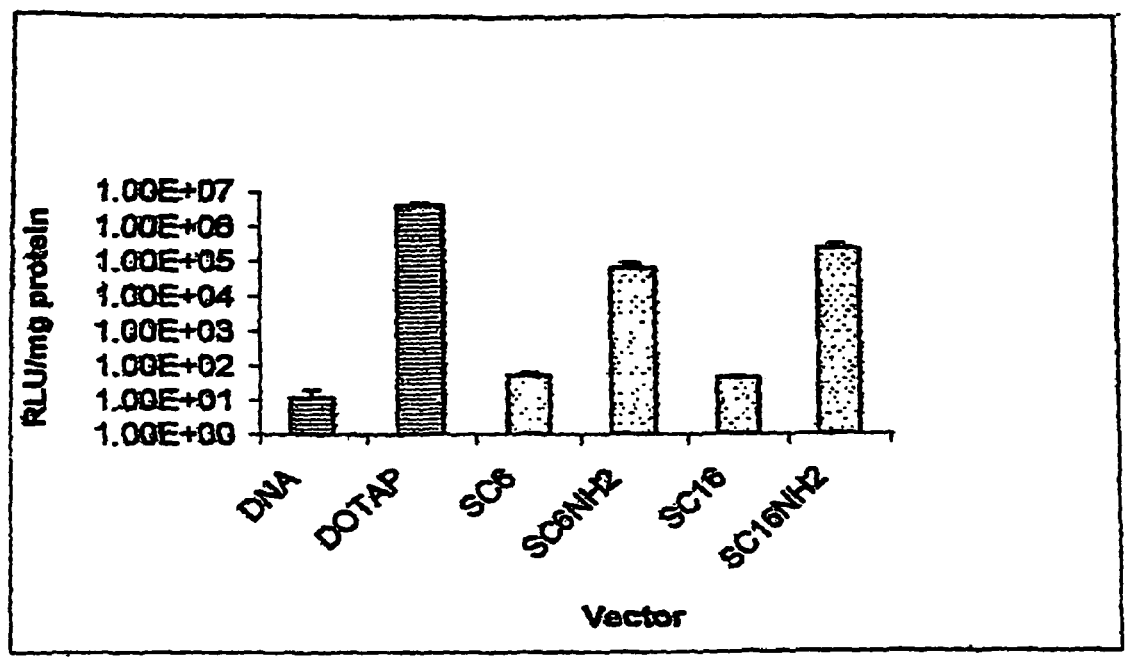

The invention will be more easily understood from the following description of some examples, given by way of reference to the accompanying figures:

FIG. 1 formula of a typical macrocyclic oligosaccharide, β-cyclodextrin,

FIG. 2 scheme of modular design of a cylindrical (a), and a wedge-shaped (b) macro-amphiphile based on a macrocyclic core, FIG. 3 electron micrograph of HE-SC$_{16}$-CD vesicles, FIG. 4 electron micrograph of HE-SC$_{12}$-CD vesicles, FIG. 5 elution of carboxyfluorescein (CF) entrapped in HE-SC$_{12}$-CD, HE-SC$_{16}$-CD vesicles, FIG. 6 release of CF from HE-SC$_{16}$-CD vesicles, and FIG. 7 comparison of transfection abilities of DOTAP and oligoethylenoxy (hydroxyethyl) cyclodextrins (HE)-SC$_6$, —SC$_6$NH$_2$, —SC$_{16}$ and —SC$_{16}$NH$_2$.

The macrocyclic oligosaccharide molecules are amphiphilic, with lipophilic groups on one face of the macrocycle, and polar hydrophilic groups on the other face. The relative effective volumes of the combined lipophilic and polar groups at either side of the molecule determine the shape of the amphiphile (FIG. 2), which in turn determines the geometry of its self-assembly (J. Israelachvili, Intermolecular and Surface Forces, 2nd Edn., Academic Press, 1991, Chapter 17). Those with relatively small or few lipophilic groups and many or large polar groups are wedge-shaped and tend to form micelles, in which the larger polar ends of the molecules are turned outwards towards the solvent and the smaller lipophilic ends are turned inwards, away from the solvent. In contrast, derivatives with lipophilic and polar ends of comparable effective volumes are cylinder-shaped and tend to form bilayers, which close into vesicles with one or more bilayered walls. (Those with a large lipophilic end and a small polar end form inverted micellar phases in nonpolar solvents.) These modifications make possible the inclusion of guest molecules not only within the macrocycle cavities, but also within the lipophilic and aqueous interiors of the molecular assemblies.

EXAMPLES

Example 1 illustrates the introduction of lipophilic groups onto one side (the primary side) of a cyclodextrin molecule. Examples 2 and 3 illustrate the introduction of hydroxyethyl (oligoethylenoxy) groups as polar groups onto the other side (the secondary side) of the molecule. Example 4 illustrates the preparation of a lyotropic phase of amphiphilic cyclodextrin; preparation of a complex of this with a hydrophilic (water-soluble)host molecule, carboxyfluorescein; and confirmation that the lifetime of entrapment is greater than three days. Example 5 illustrates the formation of a complex with a lipophilic guest molecule, an azadipyrromethene. Example 6 illustrates the preparation of a polyamino (polycationic) cyclodextrin amphiphile. Example 7 describes the synthesis of a cyclodextrin bola amphiphile. Example 8 illustrates the use of a cyclodextrin amphiphile in delivery of a guest molecule (plasmid DNA) to the interior of biological cells, as measured by resulting transfection.

Example 1

Preparation of heptakis(6-hexylthio)-β-cyclodextrin

A solution of hexanethiol (11 g, 93 mmol) in dry dimethylformamide was stirred under an atmosphere of nitrogen and with exclusion of moisture during addition of potassium tert-butoxide (10.5 g, 93 mmol). After 30 min, heptakis(6-bromo-6-deoxy)-β-cyclodextrin (7 g, 4.4 mmol) (prepared by the method of Gadelle and Defaye, Angewandte Chemie, Int. Ed. Engl., 1991, 30, 78) was added. The reaction mixture was stirred at 80° C. (5 days), then cooled and poured into an excess of water. The precipitated product was filtered off, washed repeatedly with water, then methanol, and finally stirred in hexane before filtration and drying under vacuum (10 h). Yield was 5.7 g (70%), m.p. 278° C. (decomp.).

$^1$H NMR (270 MHz, CDCl$_3$): δ 6.72 (d, J=6.4 Hz, OH-2), 5.25 (s, OH-3), 4.97 (d, J=3.1 Hz, H-1), 4.03-3.89 (m, H-3, H-5), 3.74 (m, H-2), 3.49 (m, H-4), 3.07 (m, H-6a), 2.89 (m, H-6b), 2.61 (t, SCH$_2$), 1.57-1.29, (m, CH$_2$'), 0.89 (t, CH$_3$) ppm. $^{13}$C NMR (270 MHz, DMSO-d$_6$): δ 105.9 (C-1), 88.7 (C-4), 76.6, 76.2, 75.5 (C-3, C-2, C-5), 37.4-32.0 (Cs of alkyl chain), 26.0 (C-6) ppm. Microanalysis: calculated for (C$_{12}$H$_{22}$O$_4$S)$_7$, C, 54.94; H, 8.45; S, 12.22. found, C, 55.9; H, 8.95; S, 12.35%.

Example 2

Preparation of heptakis(6-dodecylthio-2-oligoethylenoxy)-β-cyclodextrin (HE-SC$_{12}$)

Heptakis(6-dodecylthio)-β-cyclodextrin (500 mg, 200 mmol), 50 mg of K$_2$CO$_3$ and 1.00 g of ethylene carbonate (56 eq.) were mixed in 5 mL of tetramethylurea. The K$_2$CO$_3$ did not completely dissolve. The reaction mixture was stirred at 150° C. for 4 hours. At the end of this period, TLC (silica, CHCl$_3$/MeOH/H$_2$O 50/10/1) indicated complete conversion of the starting material with R$_f$ 0 and formation of a single product with R$_f$ 0.5. Furthermore, CO$_2$ emission had ceased. The reaction mixture was cooled to room temperature and the solvent was removed by rotary evaporation at 100° C. The crude product was isolated as a brown viscous oil, which was taken up in 2 mL of methanol and purified by size-exclusion chromatography through a column of 8 g of lipophilic Sephadex LH 20-100 using methanol as eluent. Product (560 mg, 184 mmol, 89% yield) was isolated as a yellow wax.

$^1$H-NMR (CDCl$_3$): δ 5.05 (br, 7H, H-1), 3.4-4.0 (m, 84H, H-2, H-3, H-4, H-5 and 14×OCH$_2$CH$_2$O), 3.00 (m, 14H, H-6), 2.60 (m, 14H, SCH$_2$), 1.60 (m, 14H, CH$_2$), 1.27 (br s, 126H, CH$_2$), 0.89 (t, 21H, CH$_3$) ppm. $^{13}$C-NMR (CDCl$_3$): δ 13.9 (CH$_3$), 22.4 (CH$_2$), 28.8 (CH$_2$), 29.2 (CH$_2$), 29.5 ((CH$_2$)$_n$), 31.7 (CH$_2$), 33.4 (CH$_2$S), 33.4 (C-6), 61.2 (CH$_2$OH), 70.5-72.0 (C-2, C-3, C-5), 72.2 (CH$_2$O), 81.0 (C-4), 100.7 (C-1) ppm. Microanalysis: calculated for (C$_{22}$H$_{42}$O$_6$S)$_7$, C, 60.83; H, 9.68; S, 7.37. found C, 60.12; H, 9.38; S, 7.62%. Electrospray MS: series of m/z from 2890 for deca(ethylenoxy) product to 3067 (MNa$^+$).

Example 3

Preparation of heptakis(6-hexadecylthio-2-oligoethylenoxy)-β-cyclodextrin (HE-SC$_{16}$)

This product was obtained from 600 mg of heptakis(6-hexadecylthio)-β-cyclodextrin (213 mmol), 60 mg of K$_2$CO$_3$ and 1.05 g of ethylene carbonate (56 eq.) in 6 mL of tetramethylurea as described for the synthesis of heptakis(2,3-hydroxyethyl, 6-thiododecyl)-β-cyclodextrin. The crude product was purified by crystallisation from 25 mL of methanol containing 20% acetone and isolated in 71% yield as brown-white powder.

$^1$H-NMR (CDCl$_3$): δ 5.05 (br, 7H, H-1), 3.4-4.0 (m, 84H, H-2, H-3, H-4, H-5 and 14×OCH$_2$CH$_2$O), 3.00 (m, 14H, H-6), 2.60 (m, 14H, SCH2), 2.00 (br, OH) 1.57 (m, 14H, CH2), 1.30 (br s, 182H, CH$_2$), 0.88 (t, 21H, CH$_3$) ppm. $^{13}$C-NMR (CDCl$_3$): δ 14.1 (CH$_3$), 22.7 (CH$_2$), 29.2 (CH$_2$), 29.4 (CH$_2$), 29.5 (CH$_2$), 29.7 (CH$_2$), 29.8 ((CH$_2$)n), 32.0 (CH$_2$), 33.7 (CH$_2$S), 34.1 (C-6), 61.5 (CH$_2$OH), 71.0-72.5 (C-2, C-3, C-5), 72.6 (CH$_2$O), 81.2 (C-4), 100.9 (C-1) ppm. Microanalysis: calculated for (C$_{24}$H$_{50}$O$_6$S)$_7$, C, 63.67; H, 10.20; S, 6.53. found C, 62.90; H, 9.47; S, 6.77%. Electrospray MS: series of m/z from 3196 for octa(ethylenoxy) product to 3458 (MNa$^+$).

Properties of heptakis(6-dodecylthio-2-oligoethylenoxy)-β-cyclodextrin and heptakis(6-hexadecylthio-2-oligoethylenoxy)-β-cyclodextrin in water are as follows.

The amphiphilic cyclodextrins are dispersed in water by sonication of a thin film (cast by slow rotary evaporation of a solution of the cyclodextrins in chloroform) in a sonication bath. HE-SC$_{12}$ is sonicated for 2 hours at room temperature and HE-SC$_{16}$ is sonicated for 2 hours at 50° C. Dynamic light scattering indicates the presence of vesicles with an average diameter of 170 nm. Vesicles of cyclodextrins of 50-300 nm diameter are also observed by transmission electron microscopy using uranyl acetate as a negative staining agent (FIG. 1). Upon prolonged sonication (9 hours) of a solution of HE-SC$_{12}$, a monodisperse solution of spherical vesicles with an average diameter of 60 nm is obtained (FIG. 2). Thus, the particle size can be directed by sonication time, in order to obtain a size suitable for specific molecular inclusion or specific therapeutic use.

Heptakis(6-hexadecylthio-2-oligoethylenoxy)-β-cyclodextrin was analysed using differential scanning calorimetry. The heating scan in differential scanning calorimetry (DSC) displayed a highly reproducible endothermic phase transition of a 10% (w/w) dispersion in water. The transition occurred around 48-49° C. and the enthalpy of transition amounted to 59 kJ/mol cyclodextrin. This typical L$_β$-L$_□$ transition was confirmed in a measurement of the fluorescence polarisation of diphenylhexatriene in the presence of a vesicle solution by a standard method (R. R. C. New, Liposomes: a practical approach, Oxford University Press, 1990). Thus, vesicles of the amphiphilic cyclodextrins undergo thermotropic phase transitions which depend on molecular structure, and which can direct important parameters such as vesicle stability and bilayer permeability.

Example 4

Preparation of Vesicles of Amphiphilic Cyclodextrin Containing Carboxyfluorescein Vesicles of heptakis(6-dodecylthio-2-oligoethylenoxy)-β-cyclodextrin and heptakis(6-dodecylthio-2-oligoethylenoxy)-β-cyclodextrin were prepared by sonication in a buffered solution of carboxyfluorescein (CF). The entrapment of CF in the internal aqueous compartment of the cyclodextrin vesicles was confirmed as follows in two independent experiments, (i) and (ii); and in experiment (iii) the lifetime of entrapment was shown to be greater than three days.

(i) Small aliquots of the solutions of the cyclodextrin vesicles (5-20 mM) were diluted 1000-fold, resulting in immediate dilution of the non-entrapped CF with concomitant intense CF fluorescence, which was measured. The fluorescence of entrapped CF is negligible due to self-quenching. Next, the vesicles in the diluted solution were solubilised by the addition of 0.1% w/w of the detergent Triton X-100, leading to release and dilution of entrapped CF, with concomitant increase of CF fluorescence, which was measured. In this concentration range (ca. 20 mM). The fluorescence intensity of CF correlates linearly with its concentration, and the incremental change of fluorescence upon addition of Triton X-100 is a direct measure of the percentage of entrapped volume of the vesicles relative to the total volume of the solution. The entrapped volume amounted to 7.7+/−1.9% and 11.4+/−2.7% for two independent preparations of HE-SC$_{16}$; and to 5.0+/−2.4% and 7.2+/−5.3% for two independent preparations of HE-SC$_{12}$.

(ii) CF entrapped in the vesicles was separated from free (non-entrapped) CF by gel filtration using Sephadex G25. Independent turbidity measurements indicated that vesicles of HE-SC$_{12}$ and of HE-SC$_{16}$ elute much faster than free CF. The peak of entrapped CF coincided with the elution of vesicles (FIG. 4). This confirms the existence of an aqueous inner compartment within the vesicles. Furthermore, as anticipated, the amount of entrapped CF in cyclodextrin vesicles correlated with the cyclodextrin concentration.

(iii) The spontaneous release of CF from vesicles of HE-SC$_{16}$ (separated from free CF by gel filtration) was measured over time. At room temperature, the leakage of CF was limited, and the vesicles retained more than 75% of CF after 3 days (FIG. 5).

These experiments demonstrate that the macrocyclic oligosaccharide vesicles can encapsulate and retain significant amounts of hydrophilic guest molecules in their compartment.

Example 5

Encapsulation of a Lipophilic (Water-Insoluble) Azadipyrromethene in Vesicles of HE-SC$_6$Cyclodextrin Solutions of azadipyrromethene (fixed concentration) and HE-CD (various concentrations) were prepared as follows: for a solution containing 0.05 mg/ml HE-CD, the HE-CD (20 μl of a 25 mg/ml soln. in chloroform), HE-CD-F (fluorescently labelled with methylanthranilate) (10 μl of a 0.5 mg/ml soln. in chloroform) and the azadipyrromethene (100 μl of a 20 mM soln. in methanol) were combined in a small vial, and the solvents were evaporated in a stream of nitrogen. Then HEPES buffer (10 mM, 1 ml) was added before sonication (1 h at 60° C.). Fluorescence of the cyclodextrin and absorbance of the dissolved (complexed) azadipyrromethene were measured, and again after one week. Table 1 below (Encapsulation of an azadipyrromethene in vesicles of HE-SC$_{16}$ amphiphile) shows that the lipophilic guest was efficiently dissolved in water by complexation with the vesicle bilayer and/or within the cyclodextrin molecular cavities.

Example 6

Synthesis of heptakis[2-(ω-amino-oligoethylenoxy)-6-deoxy-6-hexylthiol]-β-cyclodextrin (i) Preparation of heptakis[2-(ω-azido-oligoethylenoxy)-6-deoxy-6-hexylthiol]-β-cyclodextrin Heptakis[6-deoxy-6-hexylthio-2-($\overline{\omega}$-iodo-oligoethylenoxy)]-β-cyclodextrin (620 mg, 0.19 mmol) (prepared by the method of Mazzaglia et al., Eur. J. Org. Chem., 2001, 1715-1721) in anhydrous dimethylformamide (25 ml) with sodium azide (625 mg, 9.5 mmol) was stirred at 100° C. (6 days). The reaction mixture was cooled, undissolved sodium azide was filtered off, and solvent was evaporated under vacuum. The organic residue was dissolved in chloroform and insoluble material was filtered off. Evaporation of the chloroform gave crystalline product (300 mg, 60% yield).

$^1$H-NMR (CDCl$_3$): δ 5.07 (br, H-1), 3.5-4.2 (m, H-2, H-3, H-5, OCH$_2$), 3.2-3.5 (m, H-4, CH$_2$N$_3$), 2.7-2.9 (m, H-6), 2.59 (m, SCH$_2$), 1.57 (m, CH$_2$), 1.29 (m, CH$_2$), 0.89 (t, CH$_3$) ppm. $^{13}$C-NMR (CDCl$_3$): δ 14.1 (CH$_3$), 22.6 (CH$_2$), 28.7 (CH$_2$), 29.7 (CH$_2$), 31.6 (CH$_2$), 33.8 (CH$_2$S, C-6), 50.8 (CH$_2$N$_3$), 70.0-71.9 (C-3, C-5, OCH$_2$), 80.9 (C-2, C-4), 101.2 (C-1) ppm. Microanalysis: calculated for (C$_{16}$H$_{29}$O$_5$SN$_3$)$_7$, C, 51.18; H, 7.78; N, 11.19; S, 8.54. found, C, 50.07; H, 7.67; N, 10.14; S, 7.69%.

(i) Preparation of heptakis[2-(ω-amino-oligoethylenoxy)-6-deoxy-6-hexylthiol]-β-cyclodextrin Heptakis[2-(ω-azido-oligoethylenoxy)-6-deoxy-6-hexylthio]-β-cyclodextrin (vacuum-dried) in anhydrous dimethylformamide (20 ml) with triphenylphosphine (1.4 g, 5.3 mmol) was stirred under nitrogen at room temperature (5 h). The reaction solution was then maintained at 50° C. during dropwise addition over 30 min of concentrated ammonium hydroxide solution (8 ml). The reduction was complete after 24 h at 45° C. as judged by thin-layer chromatography (silica, CHCl$_3$-MeOH 5:1) which showed disappearance of starting compound. The reaction mixture was concentrated to a small volume under vacuum before precipitation of phosphorus compounds by addition of water (70 ml) and filtration. The filtrate pH was adjusted to 2 by addition of HCl (1M), and evaporation under vacuum gave crude product which was extracted with boiling hexane in a Soxhlet extractor to remove remaining phosphorus compounds. Yield of the polyamine hydrochloride salt was 385 mg (56%).

$^1$H-NMR (DMSO-d$_6$): δ 8.2 (br s, NH$_3$), 5.09 (br, H-1), 3.45-4.00 (m, H-2, H-3, H-5, OCH$_2$), 3.36 (m, H-4), 2.98 (m, H-6), 2.58 (m, SCH$_2$), 1.55 (m, CH$_2$), 1.25-1.32 (m, CH$_2$), 0.85 (t, CH$_3$) ppm. $^{13}$C-NMR (DMSO-d$_6$) 14.1 (CH$_3$), 22.9 (CH$_2$), 28.9 (CH$_2$), 29.6 (CH$_2$), 31.3 (CH$_2$), 33.7 (C-6, SCH$_2$), 39.9 (CH$_2$NH$_3$), 70.5-73.0 (C-3, C-5, OCH$_2$), 80.1 (C-2, C-4), 101.7 (C-1) ppm. Microanalysis: calculated for $(C_{16}H_{32}O_5NSCl)_7$, C, 49.87; H, 8.36; N, 3.63; S, 8.31, Cl, 9.18. found, C, 48.94; H, 7.58; N, 3.80; S, 8.03, Cl, 8.21%.

Example 7

Synthesis of heptakis[6-(12'-amino-dodecanoy-lamino)-6-deoxy-2-oligoethylenoxy]-β-cyclodextrin (i) Preparation of heptakis(6-azido-6-deoxy-2-oligo-ethylenoxy)-β-cyclodextrin Heptakis(6-azido-6-deoxy)-β-cyclodextrin (2 g, 1.5 mmol) (prepared by the method of Parrot-Lopez et al., J. Am. Chem. Soc., 1992, 114, 5479-5480) was dissolved in tetramethylurea (23 ml) and potassium carbonate (0.2 g) and ethylene carbonate (6.7 g, 76 mmol) were added. The reaction mixture was heated to 150° C. (4 h), at which time TLC analysis (silica, $CHCl_3$-MeOH 5:1) showed the reaction to be complete. Solvent was evaporated under vacuum, the residue dried overnight under vacuum, and the product purified by size-exclusion chromatography (Sephadex LH-20, MeOH).

$^1$NMR (DMSO-$d_6$): δ 3.20-3.80 (m, H-2, H-3, H-4, H-5, OCH2), 4.53 (br, H-1) ppm. MALDI-MS: series of m/z from 1774 for deca(ethylenoxy) product to 1950 ($MNa^+$).

(ii) Preparation of heptakis[6-(12'-amino-dodecanoy-lamino)-6-deoxy-2-oligoethylenoxy]-β-cyclodextrin trifluoroacetic acid salt Heptakis(6-azido-6-deoxy-2-oligoethylenoxy)-β-cyclodextrin (0.183 g, 0.01 mmol) in methanol (10 ml) with triphenylphosphine (0.56 g, 2.13 mmol), was stirred at room temperature (2 h). Concentrated aqueous ammonia (40 ml) was then added, and stirring continued (22 h). The solution was evaporated under vacuum and the residue stirred with water (10 min). After acidification to pH1 with hydrochloric acid (1 molar) and filtration, the filtrate was evaporated under vacuum. The residue was stirred with hexane (10 ml), filtered off, redissolved in water (50 ml), concentrated under vacuum, and purified by size-exclusion chromatography (Sephadex G-25, water). The reduction product, heptakis(6-amino-6-deoxy-2-oligoethylenoxy)-β-cyclodextrin (180 mg, 0.08 mmol) in DMF (10-ml) and N-ethylmorpholine (85 μl, 0.08 mmol) was treated after 1 h with a solution of activated aminoacid prepared as follows: 12'-N-tert-butyloxycarbony-lamino-dodecanoic acid (250 mg, 0.08 mmol) in dry DMF (10 ml) with dicyclohexylcarbodiimide (165 mg, 0.08 mmol) and 4A molecular sieves, was stirred at 0° C. (1 h) and then at room temperature (1 h). The combined solutions were stirred at room temperature (4 days), then filtered through Celite 520 and evaporated under vacuum to a brown residue. This was dissolved in methanol and purified by size-exclusion chromatography (Sephadex LH-20, methanol). The product was dissolved in methanol (10 ml) and trifluoroacetic acid (2 ml) was added before stirring at room temperature (1 h). The solution was evaporated to yield the product as the trifluoroacetic acid salt. MALDI-MS (free amine): series of m/z from 2805 for deca(ethylenoxy) product to 2981 ($MNa^+$).

Example 8

DNA Encapsulation, and Cell Transfection

The amphiphilic cyclodextrin vesicles were formulated as follows: the CD was dissolved in chloroform; solvent was removed by a stream of nitrogen to leave a film which was hydrated with doubly distilled deionised water. DNA (pCM-Vluc plasmid) was encapsulated by either mixing a solution of DNA with a quantity of preformed vesicles or by reconstitution of the dry CD film with a DNA solution using the optimum mass ratio CD:DNA of 10:1, followed by sonication for size reduction. Transfection studies were carried out in Day1 COS-7 cells. CD-DNA complexes were added to the cells, at a DNA dose of 1 □g per well, for 4 hours in the presence of serum free Opti-MEM, after which time serum-containing medium was added and cells were cultured for a further 20 hours. Media were replaced with fresh media and the cells were allowed express for a further 24 hours before the level of luciferase expression was determined using a Promega Luciferase Assay Kit and standardised for protein using the Biorad Dc Protein Assay Kit. The results (FIG. 7) show that the CDs cause a significant increase in transfection compared with uncomplexed DNA, and can approach the commercial vector DOTAP in efficiency. The amphiphilic CDs therefore can deliver a drug, DNA for example, into biological cells.

It is believed that one skilled in the art can, based on the description herein, utilise the present invention to its fullest extent. The above specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs.

The invention claimed is:

1. An amphiphilic macrocyclic derivative, characterised in that the macrocyclic derivative is a cyclodextrin derivative of the following formula:

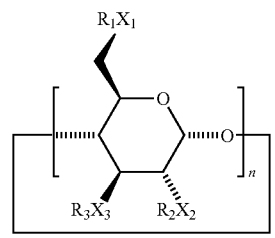

in which n equals 6-8, and indicates the number of modified glucose units in the macrocycle which are the same or different, depending on the X- and R-groups, $X_1, X_2, X_3$ independently, provide linking groups;

$R_1$ independently, provide groups which are lipophilic; and $R_2$ and $R_3$, independently, provide groups which are polar and/or capable of hydrogen-bonding, and are selected from the group comprising: $(CH_2)_{2-4}OH$, $CH_2CH(OH)CH_2OH$, $CH_2CH(OH)CH_2NH_2$, $CH_2CH_2NH_2$, a cation, an anion, sulfate, sulfonato, any pharmaceutically acceptable ion, a polyamino acid, a peptide, an oligosaccharide, and a predominantly hydrophilic group;

wherein at least one of $R_2$, and $R_3$ is wholly or in part an oligo/poly(ethyleneoxy) entity.

2. The derivative as claimed in claim 1 wherein the total size of the lipophilic groups at the 6-positions and the total size of the hydrophilic groups at the 2- and 3-positions allow self-assembly of the cyclodextrin derivative to form micelles or vesicles in aqueous solution.

3. The derivative as claimed in claim 1 wherein $X_1, X_2, X_3$ independently are a simple covalent bond or an atom or radical with a valency of at least two.

4. The derivative as claimed in claim 3 wherein the radical is selected from the group consisting of: O, S, Se, N, P, $CH_2$, $CH_2O$, carbonyl, ester, amido, amino, phosphate, sulfonyl, sulfoxide.

5. The derivative as claimed in claim 1 wherein $R_1$ is selected from the group consisting of: H, a saturated or unsaturated aliphatic or aromatic carbon or silicon radical or a halogenated version of these.

6. The derivative as claimed in claim 1 wherein the amphiphilic macrocycles are mixed with other molecules.

7. The derivative as claimed in claim 6 wherein the other molecules are selected to modulate the properties of the macrocycle assemblies.

8. The derivative as claimed in claim 7 wherein the modulatory molecules are ceramides or glycerides.

9. The derivative as claimed in claim 6 wherein the amphiphilic macrocycles form a complex with a guest molecule.

10. The derivative as claimed in claim 9 wherein the guest molecule forms a complex with the amphiphilic macrocycle for formulation into pharmaceutical compositions useful for the treatment of human or animal diseases.

11. The derivative as claimed in claim 9 wherein the guest molecules that complex with the amphiphilic macrocycle are of a lipophilic nature.

12. The derivative as claimed in claim 9 wherein the guest molecules that complex with the amphiphilic macrocycle are of a polar nature.

13. The derivative as claimed in claim 9 wherein the guest molecule may bind in a cavity of each unit of the macrocycle, in the lipophilic interior of an assembly, in the aqueous internal compartment(s) of an amphiphile assembly, or may be complexed with the amphiphile.

14. The derivative as claimed in claim 6 wherein the amphiphilic macrocycles are complexed with a molecule or atom used for analysis or diagnosis.

15. The derivative as claimed in claim 14 wherein the amphiphilic macrocycles are complexed to a peptide antigen or an antibody; or a molecule used as a radiation sensitiser.

16. The derivative as claimed in claim 14 wherein the amphiphile is complexed with a molecule which functions as a prodrug.

17. The derivative as claimed in claim 16 wherein the prodrug is a precursor of nitric oxide.

18. The derivative as claimed in claim 9 wherein the amphiphilic macrocycles may be attached to a polymer.

19. The derivative as claimed in claim 6 wherein the amphiphilic macrocycles comprise units in a copolymer.

20. The derivative as claimed in claim 19 wherein the amphiphilic macrocycles are copolymerised within the matrix of a polylactic or polyglycolic acid.

21. The derivative as claimed in claim 9 wherein the guest molecule functions as an R-group so as to provide a precursor of the active form of the guest molecule wherein $R_1$ independently provide groups which are lipophilic, and $R_2$ and $R_3$ independently provide groups which are polar and/or capable of hydrogen-bonding.

22. The derivative as claimed in claim 9 wherein the guest molecule is therapeutic molecule.

23. The derivative as claimed in claim 6 wherein the amphiphile or its complex is present as a pharmaceutical formulation with any pharmaceutically acceptable ingredient.

24. The derivative as claimed in claim 23 wherein the pharmaceutically acceptable ingredient comprises one or more of a diluent, carrier, preservative (including anti-oxidant), binder, excipient, flavouring agent, thickener, lubricant, dispersing, wetting, surface active or isotonic agent which is compatible with the amphiphile or complex.

25. The derivative as claimed in claim 23 wherein the amphiphile or complex is dispersed in a suitable solvent, buffer, isotonic solution, emulsion, gel or lyophilised suspension.

26. A formulation comprising a derivative as claimed in claim 9 and conventional non-toxic pharmaceutically acceptable carriers, adjuvants and vehicles, wherein the formulation can be administered parenterally, orally, topically, intranasally, intraocularly, vaginally, rectally, or by inhalation spray, in dosage unit.

27. The derivative as claimed in claim 6 wherein the amphiphile or the amphiphilic macrocycles comprise pharmaceutical formulations exhibiting sustained release of a drug.

28. The amphiphilic macrocyclic derivative as claimed in claim 1, wherein at least one of $R_2$ and $R_3$ is an oligo/poly (ethyleneoxy).

29. The amphiphilic macrocyclic derivative as claimed in claim 1, wherein one of $R_2$ and $R_3$ are selected from the group comprising a polyamino acid, a peptide and an oligo saccharide.

* * * * *